United States Patent [19]

Rubens et al.

[11] Patent Number: 5,731,357
[45] Date of Patent: Mar. 24, 1998

[54] IMMUNOMODULATING ACTIVE SUBSTANCE

[76] Inventors: Juris Rubens, Brīvības 76-23, LV-1001 Rīga; Larisa Poluektova, Anninmuižas bulv. 80-13, LV-1069 Rīga; Nadežda Gromova, Dzelzava 35-44, LV-1084 Rīga; Jurijs Seleznovs, Loku magistrāle 21-97, LV-3000 Jelgava, all of Latvija, Latvia

[21] Appl. No.: 588,129

[22] Filed: Jan. 18, 1996

[51] Int. Cl.$^6$ .......................... A01N 31/00; C07C 29/00
[52] U.S. Cl. ........................ 514/739; 568/909.5
[58] Field of Search ................... 514/739; 568/909.5

[56] References Cited

U.S. PATENT DOCUMENTS

| | | | |
|---|---|---|---|
| 5,073,572 | 12/1991 | Gunasekera et al. | 514/739 |
| 5,280,048 | 1/1994 | Yamamoto et al. | 514/739 |

OTHER PUBLICATIONS

Hannus et al., Phytochemistry, 1974, vol. 13, pp. 2563–2566.
Roshehin et al., Rastitelnie Resursi, 1986, vol. 22, No. 4, pp. 530–537, English abstract.

*Primary Examiner*—Alan L. Rotman
*Assistant Examiner*—Lyman H. Smith
*Attorney, Agent, or Firm*—Abelman, Frayne & Schwab

[57] ABSTRACT

The invention is an immunomodulator-antistressant and allows to protect immune system from depressive influence of chronic emotional stress with this preventing depression in 1.25–2.5 times of immune reaction. It intensifies humoral immune reaction in 1.9–2.3 times and stimulates phagocyte activity of macrophages in 1.3–1.85 times which is especially important for treatment of immunodeficiency states.

With the presence of pathological increased immune reaction (autoimmune diseases—rheumatic arthritis, non-specific ulcerative colitis, psoriasis, chronic glomerulonephritis, etc.) it normalises it, suppressing the progress of humoral immune reaction in 4.7–11.8 times.

3 Claims, No Drawings

IMMUNOMODULATING ACTIVE SUBSTANCE

FIELD OF THE INVENTION

This invention has to do with the medicine and applies to the question of making medicinal immunomodulating active preparations.

Artificial correction of immune homeostasis, especially in the cases of acquired or genetically predetermined immune deficient states (sepsis, AIDS, etc.,) is a very actual scientific and practical task. There is a special need in those substances combined modulating properties (stimulator-depressor).

BACKGROUND OF THE INVENTION

Inosiplex (isoprinosin) belongs to such combination which is now widely used abroad as an antivirus and immunostimulating preparation, used in acquired immunodeficite syndrome treatment (AIDS) (1, 2).

However, the production of this combination is a difficult synthetic process which requires import component parts and reagents. That is why the search of new substances with immunomodulating properties derived from raw materials available by wasteless technology is of a great importance.

SUMMARY OF THE INVENTION

The elaboration of a immunomodulating active substance is the purpose of this invention.

This purpose is achieved by using as an immunomodulating active substance Ropren (Rp)-plant polyprenols with a carbon chain of fifty and more carbon atoms and has the following chemical formula:

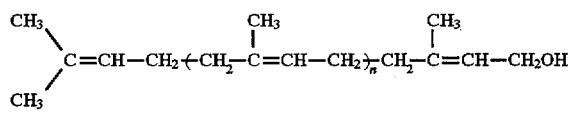

The Rp with a carbon chain of fifty and more carbon atoms are derived from needles of the fir tree, *picea abies*, or needles of the pine tree, *pinus sylvestris*.

Common symptoms for analogue of invention-inosplex (In) and proposed invention-Rp origin with carbon chain of fifty and more carbon atoms are:

1. Stimulation of forming antibody-forming cells in the spleen.
2. Stimulation of humoral immune reaction with weak-replied animals and strong-replied mice with suboptimum dose of antigen.
3. Suppress of humoral immune reaction with strong-replied animals during immunisation by optimal dose of antigen.
4. Stimulation of phagocytosis and digesting ability of macrophages.

The distinctive signs of invention and analogue of invention are:

ROPREN

1. Chemical formula and structure.
2. Derived from plant raw materials.
3. Do not possess toxicity; LD 50 is not revealed in dose of more than 10 000 mg/kg.
4. During 10 days administration inside at a dose of 100 mg/kg prevent lowering of humoral immune reaction and infringement of macrophage functions cased by emotional stress.

INOSIPLEX

1. Chemical formula and structure.
2. Derived by chemical way (synthesis).
3. Toxicity: LD 50 7 500–10 000 mg/kg.

As a result of investigations it was ascertained that Rp with a carbon chain of 50 or more carbon atoms has an immunomodulating effect on the development of both cell and humoral immunity. LD 50 for Rp with a carbon chain of fifty or more carbon atoms, determined on white mangrel mice during oral administration, is not revealed in dose more than 10 000 mg/kg.

Immunomodulating activity of the Rp was experimentally investigated in line animals having genetically predetermined immune disbalance/mice reefing to lines C57B1/6 CBA, and F1 (CBA×C57B1/6/ /1/.

Emulsion of the Rp was prepared in 0.025-percent Tween-80 solution (Merck). Experimental animals were intraperitoneally administered doses of 10.0 and 100.0 mg/kg in 0.1 ml in parallel to antigen administration; similar doses were given per os for 5 days before antigen administration. 0.025-percent Tween-80 solution was used as an intraperitoneal control exerting no direct effect on antibody-forming cell count in mouse spleen, delayed skin reaction (DSR), graft-versus-host reaction (GVHR) or phagocytosis, while causing slight stimulation of antibody production (activity index 1.2); persic oil was used as a per os administration control leading to no alterations in the immune system /2,3/.

Experimental emotional stress was created by overcrowding (40 mice in a 17×25×8 cm cage) for 10 days. during the experiment, control animals were daily given per os doses of Tween-80 solution, and experimental animals were intraperitoneally administered RSL-1/88-1 "BF" at a dose of 100.0 mg/kg /4,5/.

In was dissolved in physiological solution and administered intraperitonerally at single doses together with antigen (sheep erytrcytes). Physiological solution was used as a control. In was administered at doses of 0.5 to 250.0 mg/kg.

The following investigative techniques were used to determine the effects produced by the substances under study on animals immune system:

1. Determination of antibody-forming cell cont in mouse spleen on the 5th day following immunization using optimum ($1\times10^8$ cells) and suboptimum ($2\times10^7$ cells) doses of sheep erythrocytes, i.e. local hemolysis reaction /6/.
2. Determination of hemagglutinin titers for sheep erythrocytes on the 7th and 14th days following immunization with the optimum and suboptimum doses, using 96-hole round-bottom pans. Results were accounted for macroscopically and expressed in log2 of a titer. Adminisration patterns used were similar to those practiced when determining antibody-forming cell counts /7/.
3. DSR deermination using intravenous immunization of mice with sheep erythrocytes administered at a dose of $2\times10^5$ cells. A resolution dose ($1\times10^8$ cells in 0.04 ml of physiological solution) was injected in a hind footpad on the 5th day following immunization. Local inflammatory reaction was accounted for 24 hours later by the difference of mass between experimental (Re) and control (Rc) footpads. Reaction index (RI) was calculated for each mouse using the following formula:

$$RI = \frac{Re - Rc}{Rc} \times 100\% \quad /8/$$

4. GVHR determination. GVHR was induced by subcutaneous administration of $2\times10^6$ lymph node cells of host genotype (CBA) into right hind footpads of line F1

(CBA×C57B1/6) mice. Syngeneic lymphocytes were administered into left footpads. Cell count was determined in 5 ml of homogenate of left (control) and right (experiment) lymph nodes.

Reaction index (RI) was calculated using the following formula:

$$RI = \frac{control}{experiment} \qquad /9/$$

Administrations were performed via the intraperitoneal route simultaneously with GVHR induction.

5. Estimation of phagocytic activity of peritoneal macrophages in mice, using JgG-opsonized sheep erythrocytes as the phagocytosis target /10/. Macrophages were attracted by 4-percent hydrolyzed starch solution. On the 3rd or 4th day, 0.5 ml of 5-percent sheep erythrocyte suspension were administered intraperitoneally. Following 60 minutes, exudate was removed. Non phagocytic sheep erythrocytes were subjected to lysis. Cell suspension was washed out. The preparation stained per Romanovsky-Gimze was determined for phagocyting cell percentage. To determine phagocytic index (PI1), the number of sheep erythroccytes captured was calculated spectrophotometrically /11/ by hemoglobin concentration using a calibration curve. Phagocytic index (PI2) was determined again following 3 hours of incubation at 37° C. Phagocytosis completion index (PCI) was calculatd using the following formula:

$$PCI = \frac{PI1 - PI2}{PI2} \times 100\%$$

Phagocytic activity determination in vivo in mice by intravenous injection of 25-percent ink solution at an amount of 0.5 ml. Then, for 15 minutes blood was taken from orbital sinus (0.020 ml) every 3 minutes and introduced into 1 ml of 3-percent acetic acid. Blood taking completed, animals were killed and body weight, liver and spleen weight were measured. Optical density of hemolyzed blood determined spectrophometrically at 610 nm wavelenght, and the f (D) t curve was plotted. Points lg (0) (zero time) and lg(10) (on the curve) were located. Phagocytosys constant (K) was calculated using the following formula:

$$K = \frac{lg0 - lg10}{lg10}$$

and then true phagocytosis index ($\alpha$) was calculated using the following formula:

$$\alpha = \frac{body\ weight}{liver\ weight + spleen\ weight} \times \sqrt[3]{K} \qquad /2/$$

7. Complement activity determination using the titration technique employing rabbit erythrocytes treated with hyperimmune antiserum of guinea pig /12/ for direct activation route and employing rabbit erythrocytes treated with potassium iodide solution /13/ for alternative activation route. Activity was expressed in units 50-percent lysis per ml of serum (CH50).

8. Statistical processing of data thus obtained was performed on a digital computer using an application program package. Student's and Whitney-Mann-Wilcoxon technique were applied. Logarithmic indices were used for data processing of antibody-forming cell counts and hemagglutinin titers.

RESULTS

1. Effects exerted by Rp and In on humoral immune response development

Investigative data concerning Rp effect on antibody-forming cell formation in mouse spleen and on hemagglutinin titers in serum of various line mice immunised with the optimum and suboptimum doses of sheep erythrocytes are summarised in Tables 1 and 3. As can be seen from these tables, when administered intraperitoneally Rp leads to approximately 2 fold production of antibody-forming cells in spleen and to two times higher hemagglutinin level in serum of line C57B1/6 mice that are low-responsive to sheep erythrocytes, when immunised with optimum or suboptimum antigen doses. More intensive production of antibody-forming cells in high-responsive mice F1 in the suboptimum immunisation mode with Rp administered at doses of 10.0 and 100.0 mg/kg, and higher hemagglutinin titers with Rp administered at a dose of 100.0 mg/kg indicate the presence of adjuvant properties.

With Rp administered at a dose of 100.0 mg/kg for 5 days, antibody-forming cell counts in spleen of line C57B1/6 mice increased both in the optimum and suboptimum immunisation modes, whereas hemagglutinin titers increased in the optimum immunisation mode only.

It is of interest to note the very fact of dose-dependent depression of antibody-forming cell production in spleen of line F1 mice with sheep erythrocytes administered at the optimum dose (Table 1), and decrease of hemagglutinin titers in serum with Rp administered at a dose of 100.0 mg/kg via intraperitoneral or per os route. This phenomenon might be related to simultaneous administration of considerable amounts of sheep erythrocytes and substance Rp activating a respiratory enzyme chain /14/ as well as monooxygenases, e.g. cytochrome P-450 /15/. The latter circumstance related to functional conjunction between the immune system and metabolism leads to accelerated degradation of erythrocytes in phagocyting cells, weaker antigenic properties of sheep erythrocytes and thus, less pronounced humoral immune response in intact animals with high-quality physiological parameters. According to literature data, similar immunodepressive properties are exhibited by alkyl- and aryl-substituted 5-oxypyrimidines /16/, 3-oxypyridine derivatives, and aqueous extracts of pea tissues /17/.

As can be seen from Table 3, decrease in hemagglutinin titers is of phasewise character; no valid difference can be detected in experimental and control group indices by the 14th day following immunisation.

Thus, a conclusion can be made that vegetable origin substance Rp stimulates development of humoral immune response, possesses adjuvant properties, and modulates the degree of humoral immune response in high-responsive line mice.

A series of experiments was set up to investigate In effect on production of antibody-forming cells in spleen of line mice that are opposite responsive to T-dependant antigen, i.e. sheep erythrocytes (see Table 1); three dosage values (0.5, 5.0 and 50.0 mg/kg) and two immunization modes (optimum and suboptimum) were used. As can be seen from Table 2, when given at a dose of 0.5 mg/kg in the optimum immunization mode only, inosiplex intensifies formation of antibody-producing cells by 90 percent (p 0.05) in low-response line C57B1/6 mice.

When given at a dose of 5.0 mg/kg in the suboptimum immunisation mode, In induces poorly expressed and statistically invalid effect increasing antibody-forming cell count by 38 percent. In the optimum immunisation mode, it increases antibody-forming cell count by 82 percent (p 0.05).

When given to low responsive line mice at a dose of 50.0 mg/kg in the suboptimum and optimum immunisation modes, the stimulating effect of inosiplex amounts to 32 and 139 percent, respectively.

A series of experiments was set up to investigate inosiplex effect on the antibody formation level (hemagglutinin titer for sheep erythrocytes) in the suboptimum T-dependent antigen immunisation of mice, with inosiplex administered at doses of 0.5, 5.0, 25.0, 50.0, and 250.0 mg/kg.

When In was given at doses of 0.5, 5.0 and 25.0 mg/kg to line CBA mice, no stimulating effect (p 0.05) was observed both on the 7th and 14th day following immunisation (see Table 4).

When given at a dose of 250.0 mg/kg (Table 4), inosiplex stimulated hemagglutinin production as much as two times (1 log2 of hemagglutinin titer).

2. Effects exerted by Rp and by In on cell immune response development

Data concerning Rp effect on DSR and GVHR are summarised in Table 5. As can be seen from this table, this substance induces no changes in cell-type reaction rates when administered at a single intraperitoneal doses. When given per os at a dose of 100 mg/kg for 5 days to line C57B1/6 mice whose DSR is 2.0 to 2.5 times more vigorous that than in line CBA mice, Rp suppresses intensity of this reaction. Per os administrations of Rp exerted no effect on GVHR development.

Investigation of In effect on DSR development was performed in mice of two lines, with the drug administered at doses of 0.5, 5.0 and 50.0 mg/kg. The drug induced no changes in the reaction intensity (see Table 6).

Investigation of In effect on GVHR was also made using doses of 0.5, 5.0 and 50.0 mg/kg. In was noted for a slight inhibitory effect when given at a dose of 50.0 mg/kg (p 0.05) (see Table 6).

3. Effects exerted by Rp and by In on phagocytic activity of macrophages

Investigative data concerning Rp effect on phagocytic activity of peritoneal macrophages and on ink clearance are summarised in Tables 7 and 9.

As can be seen from Table 7, when administered at single intraperitoneal doses Rp induces neither changes in phagocytic cell cont in peritoneal exudate nor alterations in ability of phagocytes to capture opsonized sheep erythrocytes, while causing 1.5–2.0 fold incease in digestive capacity of macrophages. When administered per os at a dose of 100.0 mg/kg, Rp increases phagocytic cell count in exudate while inducing no changes in phagocytic index or in phagocytoosis completion index. When administered intraperitoneally, Rp is able to stimulate phagocytosis completion; this can be related to the local effect of the substance.

When administered intraperitoneally or per os, Rp induces no changes in capturing intensity of inert ink particles and exerts no influence on blood clearence rate (Table 9).

The effect of In given at doses of 0.5, 5.0 and 50.0 mg/kg on phagocytosis index was studied in hybrid line F1 (CBA× C57B1/6) mice, with he drug administered intraperitonreallly 30 minutes before injection of the phagocytosis target, i.e. sheep erythrocytes.

At a dose of 0.5 mg/kg, no stimulation effect was noted.

At a dose of 5.0 or 50.0 mg/kg, phagocytosis commpletion index increased by 39 percent (p 0.02) and 76 percent (p 0.01), respectively (see Table 8).

The effect of In on ink clearance rate (phagocytosis in vivo) was studied with the drug administered intraperitoneally at doses of 0.5, 5.0 and 50.0 mg/kg 30m minutes before intravenous ink injection.

As can be seen from Table 10, when administered intraperitoneally In induces no changes in capturing intensity of inert ink particles and exerts no effect on blood clearence rate.

4. Effects exerted by Rp on complement activity

Investigative data concerning Rp effect on the activity of mouse blood serum complement are summarised in Table 11.

As can be seen from this table, Rp exerts no effect on the activity of mouse blood serum complement.

5. Effect exerted by vegetable-origin substance Rp on immune system of stressed animals Investigative data concerning Rp effect on the degree of immune deficient state induced by emotional stress are summarised in Table 12.

As can be seen from this table, overcrowding for 10 days results in suppression of humoral immune response (antibody forming cell count and hemagglutinin count) and in suppression of phagocytosis completion and inert ink partiocle clearance rate (approximately 1.25 to 2.2 times). All these disturbances (exept for the latter) are precluded by per os administration of Rp at a dose of 100.0 mg/kg for 10 days.

Thus, per os administration of Rp protects the immune system against depressive effects of an emotional stress.

DISCUSSION

The present experimental study has resulted in the following findings. Rp causes 1.9–2.3 fold stimulation of humoral immune response development in low responsive line C57B1/6 mice when given at doses of 10.0 and 100.0 mg/kg, and in high responsive line F1 (CBA×C57B1/6) mice immunised with the suboptimum dose of antigen (sheep erythrocytes). This Rp effect can be utilised in the various bacterial origin infectious diseases, and particularly in septic cases when humoral immunity to pathologic microorganisms is considerably reduced. Combined usage of an immunostimulator and antibiotics shall yield a higher therapeutical effect.

When given doses of 5.0 and 50.0 mg/kg, In causes 1.3–1.8 fold stimulation of humoral immune response in animals that are low responsive to antigen.

When administered at doses of 10.0 and 100.0 mg/kg intraperitoneally and at a dose of 100.0 mg/kg per os to high responsive line F1 (CBA×C57B1/6) mice immunised with the suboptimum antigen dose, Rp leads to 4.7–11.8 fold suppression of humoral immune response development. This suppressive effect of Rp can be utilised for correction of pathologically enhanced humoral immune response in various allergic and autoimmune cases, such as bronchial asthma, non-specific ulcerative colitis, psoriasis, systemic lupus erythematosus, rheumatic arthritis, and the like.

When given at doses of 5.0 and 50.0 mg/kg, In also suppresses humoral immune effect in line CBA mice that are high-responsive to antigen in the optimum immunization mode, but to a lower extent than Rp (1.74 to 2.3 times).

A vital task of extreme practical importance for modern immunology is a search for biologically active substances which would be able, by effecting the immune system directly or indirectly (via the central nervous system), to protect an organism against oppressive immunodepressive effect of chronical emotional stress which is known to frequently result in various diseases (including oncological ones) due to failure of fine specific protection mechanisms. With proper consideration of the above, Rp was investigated for antistressor activity. When administered per os at a dose of 100.0 mg/kg for 10 days, Rp precluded 1.25–2.2 fold humoral immune response decrease and microphage functional disturbance as induced by chronical emotional stress.

This effect of Rp can be utilized for prophylaxis and treatment of many diseases (including oncological ones) whose significant trigger link is decreased immunological resistance due to chronic emotional stress, as well as for prophylaxis of possible recurrences. Antistressor and adaptogenic effects of Rp can be used in cases of long term psychoemotional or physical overloads, particularly under confined room conditions, e.g. in ship, polar station or during a long time space flight, etc.

When administered intraperitonealy, Rp does not affect development of cell type immune reactions, sych as DSR or GVHR. In has similar properties.

When given per os at a dose of 100.0 mg/kg for 5 days, Rp causes 1.2 fold suppression of DSR development.

The fact that Rp exerts no effect on celluar immunity while stimulating humoral immune response, can be of much practical imprtance for treating secondary immune deficient states in transplantation cases and related immunodepressive thearapy necessitating prophylaxis of bacterial sepsis.

When intraperitonealy administereds at doses of 10.0 and 100.0 mg/kg, Rp induces 1.3–1.85 fold stimulation of phagocytosis completion; when given per os at a dose of 100.0 mg/kg, it leads to a 1.3 fold increse of phagocyting cell count in peritoneal exudate.

When administered intraperitoneally at doses of 5.0 and 50.0 mg/kg, In also stimulates phagocytosis completion, but to a lesser degree than Rp (1.4–1.7 times).

Stimutlating effect of Rp on phagocytosis in combination with its stimulating effect on humoral immune response can be used for treatment of septic states and bacterial or viral.

Stimutlating effect of Rp on phagocytosis in combination with its stimulating effect on humoral immune response can be used for treatment of septic states and bacterial or viral. infections as well as for conservative action on metastases or primery tumor following radical oncological operation.

Thus, it can be concluded that Rp is a new immunomodulator which affects selectively humoral link of immune response and nonspecific phagocytic activity of microphages; therefore, it can be used in the treatment of various diseases whose principal pathogenic mechanism is disbalance of the immune system which is responsible for genetic inegrity and uniformity of an organism and for protection of the latter against living bodies or substances bearing genetically heterologous signs. In addition, Rp is an efficient antistressor and adaptogenic drug capable of protecting the immune system against depressive effects of chronic emotional stress and ensuring prophylaxis of various diseases associated with any degree of immune disbalance.

Biological investigation of Rp has shown it to be completely innocuous, to have no effect on reproductive function, to induce no undesirable mutations, and to have neither embryotoxic nor tetragonic effects.

The preparation "Ropren" is considered as a new class of low-molecular biological regulators that are transformed into dolichol in the human organism. Dolichols are long chain polyprenols containing a α-saturated isoprene unit and take part in the process of biosynthesis of polysaccharides, glicoproteins and similar biological polymers containing carbohydrates /1–3/.

The excretion of dolichols takes place through the urinary system. Normal value for urinary dolichol levels are 6–17 µg per mmole of creatinine. The necessary amount of ropren per day for adults is 6–12 mg. It is known that urinary dolichols are increased many times in cerebral neuronal lipofuscinosis, in metastatic cancer, in severe bacterial infection, in chronic alcoholics and in new-borns whose mothers were heavy drinkers /4–7/.

The purpose of this invention is to achieve the clinical remission for patients with chronic hepatitis and disseminated sclerosis by means of compensating the loss of dolichols with internal usage the preparation "Ropren".

The preparation passed all stages of the preclinical approbation and Permission 7 to conduct clinical approbation was issued by Pharmacological and Pharmacopeial Committee, Department of Pharmacy of the Latvian Ministry of Welfare (a copy certified by the notary office is enclosed).

The received data prove that the preparation "Ropren" is not toxic and harmful for the human organism.

Urinary dolichol levels were investigated using the group of patients with clinically proven chronic hepatitis (n=10) and disseminated sclerosis (n=8). The control group was made up of 10 healthy volunteers.

Raised urinary dolichol levels were revealed in the group of the patients with chronic hepatitis and disseminated sclerosis. The raised urinary dolichol levels were compensated by using the preparation "Ropren". After a while, the clinically proved remission followed.

The Treatment of Patients with Chronic Hepatitis using the Preparation "Ropren"

The treatment of chronic hepatitis by means of the preparation "Ropren" was carried out with the group of 10 patients on the basis of the double blind method, sunflowerseed oil being used as placebo. The control group consisted of 10 healthy volunteers.

Ropren and placebo, both were administrated per os for a month.

During the research, contents of bilirubin in serum, total protein, alanine aminotransferase and alkaline phosphatase were determined. The urinary dolichol levels were determined before the research, on the 10th, 20th and 30th day of the treatment and after a month of its conclusion.

The patients were clinically investigated to evaluate their state paying attention to the signs of intoxication (weakness, loss of appetite, vomiting and body temperature) and cholestasia (changes of a liver size, haemorrhage, itch and meteorism).

The data received were processed using the methods of variance statistics.

The administration of placebo for a month did not improve the functional state of liver and urinary dolichol levels remain the same.

The administration of ropren lowered urinary dolichol levels. Accordingly, the dosage was reduced as long as urinary dolichol levels went down. The dosage was calculated using the formula $$R_p = \frac{UD_2}{UD_1} \times R_n.$$

where $R_p$—required dosage $R_n$—necessary amount $UD_1$—urinary dolichol level in health $UD_2$—urinary dolichol level in disease The administration of ropren improves considerably the functional state of liver (the activity of alanine aminotrasferase increases by 30% and that of alkaline phosphatase-by 100%, the contents of protein go up by 100% and that of bilirubin by 15%). The signs of intoxication and cholestasia disappeared. The administration of placebo did not influence the functional state of liver, the signs of intoxication and cholestasia remained without changes. In the control group all indices were within the limits of physiological standards.

Conclusion. The administration of the preparation "Ropren" enables to achieve clinical remission for the patients with chronic hepatitis.

The Treatment of Patients with Disseminated Sclerosis using the Preparation "Ropren"

The treatment of disseminated sclerosis by means of the preparation "Ropren" was carried out with the group of 8 patients on the basis of the double blind method, sunflowerseed oil being used as placebo. The control group consisted of 10 healthy volunteers.

Ropren and placebo, both were administrated per os for 6 months.

The group consisted of males and females at the age of 18–40 years. The diagnosis was checked before the start using the method of magnetic resonance. For last 6 months, the patients did not get large doses of azotioprin and prednisalon and they were not suffering from heavy forms of the disease (7–10 Kurtzke numbers). During the research (before the start, after 3 months, at the end and a month after the conclusion) urinary dolichol levels were determined as well as the patients were examined in accordance with Kurtzke EDSS (Expanded Disability Status Score, 0–10 numbers). After three months of the treatment, urinary dolichol levels dropped down on the average by 4.5 times. It allowed to decrease the dosage of ropren. After 6 months urinary dolichol levels became normal and remained unchanged within a month, when administration of ropren was stopped. The state of the patients was 0.5–1.0 according to Kurtzke.

The usage of placebo did not change urinary dolichol levels. The state of the patients was 4–6 according to Kurtzke. In the control group all indices were within standards.

CONCLUSION. The administration of the preparation "Ropren" enables to achieve clinical remission for the patients with disseminated sclerosis

TABLE 1

ROPREN EFFECT ON PRODUCTION OF ANTIBODY FORMING CELLS (AFC) IN MOUSE SPLEEN

| N° | Administration route | Mouse line, sex, weight[1] | Sheep erythrocyte dose (cells) | Ropren dose (mg/kg) | AFC count per $10^6$ nucleated spleen cells | p< | AFC count per entire organ | p< |
|---|---|---|---|---|---|---|---|---|
| 1. | Single intraperitoneal dose | C57B1/6 males 22–25 g | $2 \times 10^7$ | Control 10.0 100.0 | 5.4(6.0'4.8) 11.5(13.5'9.8) 10.2)11.7'8.9) | 0.01 0.01 0.01 | 1072(1202'955) 1122(1202'1047) 1288(1479'1122) | |
| 2. | Single intraperitoneal dose | C57B1/6 females 21–22 g | $10^8$ | Control 10.0 100.0 | 5.5(6.3'4.8) 12.6(12.9'12.3) | 0.001 0.001 | 794(891'708) 1585(1820'1380) 1585(1820'1380) | 0.001 0.001 |
| 3. | Single intraperitoneal dose | $F_1$ (CBAxC57B1) males 21–23 g | $2 \times 10^7$ | Control 10.0 100.0 | 6.9(7.6'6.3) 12.6(13.2'12.0) 10.7(11.0'10.5) | 0.001 0.001 | 764(851'741) 1259(1318'1202) 1259(1288'1000) | 0.001 0.001 |
| 4. | Single intraperitoneal dose | $F_1$ (CBAxC57B1) females 21–23 g | $10^8$ | Control 10.0 100.0 | 23.7(25.1'21.9) 5.0(5.4'4.7) 2.0(2.4'1.7) | 0.001 0.001 | 3981(4541'3467) 1000(1072'933) 398(473'363) | 0.001 0.001 |
| 5. | Single intraperitoneal dose | $F_1$ (CBAxC57B1) females 21–23 g | " | Control 10.0 100.0 | 44.7(49.0'41.0) 25.1(31.0'20.4) 10.0(12.0'8.3) | 0.05 0.001 | 9772(11220'8511) 5012(5754'4365) 3981(4467'3548) | 0.02 0.001 |
| 6. | Per os, for 5 days | C57B1/6 males 18–20 | $2 \times 10^7$ | Control 10.0 100.0 | 6.3(7.9'5.0) 7.9(10.2'6.2) 15.8(18.2'13.8) | 0.05 | 794(1120'562) 1000(1230'813) 3162(3548'2818) | 0.01 |
| 7. | Per os, for 5 days | C57B1/6 females 20–22 g | $10^8$ | Control 10.0 100.0 | 5.4(6.2'4.7) 7.1(8.1'6.2) 7.8(8.5'7.1) | 0.05 | 631(794'501) 1000(1259'794) 955(1023'891) | |
| 8. | Per os, for 5 days | $F_1$ (CBAxC57B1) males 21–23 g | $2 \times 10^7$ | Control 10.0 100.0 | 16.0(17.0'15.0) 20(23.0'17.0) 16(19.0–13.012) | | 1995(2344–1698) 3162(3802'2630) 1995(2239'1778) | |
| 9. | Per os, for 5 days | $F_1$ (CBAxC57B1) males 23–25 g | " | Control 10.0 100.0 | 10.0(11.7'8.5) 12.6(14.5'11.0) 7.9(8.9'7.1) | | 1000(1072'933) 1585(1820'1380) 1175(1288'1072) | 0.02 |
| 10. | Per os, for 5 days | $F_1$ (CBAxC57B1) females 21–23 g | $10^8$ | Control 10.0 100.0 | 17.0(18.2'15.8) 11.0(13.5'8.9) 10.7(12.0'9.5) | 0.01 | 3162(3467'2884) 1996(2455'1622) 1585(1995'1259) | 0.001 |

[1]8 animals in a group

TABLE 2

INOSIPLEX EFFECT ON ANTIBODY-FORMING CELL (AFC) POOL PRODUCTION IN MOUSE SPLEEN

| Mouse line, weight, number in a group | Sheep erythrocyte dose (cells) | Drug | AFC COUNT PER $10^6$ NUCLEATED SPLEEN CELLS | | | | | |
|---|---|---|---|---|---|---|---|---|
| | | | Control | 0.5 mg/kg | stimulation degree, % | 5.0 mg/kg | stimulation degree, % | 5.0 mg/kg | stimulation degree, % |
| C57Bl/6, males, 20–22 g n = 8 | $2 \times 10^7$ $10^8$ | inosiplex inosiplex | 85(98–74) 83(102–68) | 52(63'44) 158(186'134) $p < 0.05$ | 90 | 117(149'98) 151(169'134) $p < 0.05$ | 38 82 | 112(141'89) 199(245'162) $p < 0.01$ | 32 139 |

TABLE 3

ROPREN EFFECT ON HEMAGGLUTININ (GA) TITER FOR SHEEP ERYTHROCYTES IN MOUSE SERUM[1]

| N° | Administration route | Mouse line, sex, weight | Sheep erythrocyte dose (cells) | Ropren dose (mg/kg) | HA TITERS FOLLOWING IMMUNIZATION | | | |
|---|---|---|---|---|---|---|---|---|
| | | | | | 7th day | P< | 14th day | P< |
| 1. | Single intraperitoneal dose | C57Bl/6, males. 21–23 g | $2 \times 10^7$ | Control 10.0 100.0 | 6.75)0.20 7.50)0.15 7.50)0.17 | 0.02 0.02 | 4.92)0.26 6.17).31 5.70)0.15 | 0.01 0.05 |
| 2. | Single intraperitoneal dose | C57Bl/6, males. 20–22 g | $10^8$ | Control 10.0 100.0 | 5.58)0.21 6.50)0.17 6.50)0.12 | 0.01 0.01 | 7.42)0.28 8.08)0.20 8.00)0.17 | |
| 3. | Single intraperitoneal dose | C57Bl/6, males. 20–22 g | " | Control 10.0 100.0 | 8.5)0.179 9.42)0.23 9.67)0.39 | 0.01 0.02 | 7.92)0.19 8.67)0.17 9.17)0.21 | 0.01 |
| 4. | Single intraperitoneal dose | $F_1$ (CBAxC57B1) males, 22–24 g | $2 \times 10^7$ | Control 10.0 100.0 | 7.3)0.3 7.2)0.4 8.3)0.2 | 0.02 | 8.4)0.3 7.7)0.4 9.6)0.2 | 0.01 |
| 5 | Single intraperitoneal dose | $F_1$ (CBAxC57B1) males, 22–24 g | " | Control 10.0 100.0 | 6.92)0.17 8.00)0.12 7.25)0.21 | 0.001 | 8.5)0.41 9.1)0.25 9.5)0.41 | |
| 6. | Single intraperitoneal dose | CBA, females, 18–22 g | $10^8$ | Control 10.0 100.0 | 8.5)0.45 7.6)0.25 7.3)0.13 | 0.05 | 8.5)0.32 7.3)0.22 8.0)0.31 | 0.01 |
| 7. | Single intraperitoneal dose | $F_1$ (CBAxC57B1) males, 18–20 g | " | Control 10.0 100.0 | 6.9)0.25 6.4)0.14 5.8)0.17 | 0.001 | 10.2)0.4 10.9)0.6 10.5)0.4 | 0.01 |
| 8 | Per os, for 5 days | C57Bl/6, males, 18–20 g | $2 \times 10^7$ | Control 10.0 100.0 | 8.10)0.42 7.60)0.65 7.70)0.58 | | 6.80)0.25 7.60)0.42 7.20)0.47 | |
| 9. | Per os, for 5 days | C57Bl/6, females, 21–23 g | $10^8$ | Control 10.0 100.0 | 5.80)0.12 6.70)0.25 6.80)0.20 | 0.01 0.01 | 6.10)0.09 7.30)0.30 6.30)0.20 | 0.01 |
| 10. | Per os, for 5 days | $F_1$ (CBAxC57B1) males, 20–22 g | $2 \times 10^7$ | Control 10.0 100.0 | 9.00)0.25 10.70)0.09 6.70)0.37 | 0.001 | 7.10)0.30 7.30)0.30 7.30)0.30 | |
| 11. | Per os, for 5 days | $F_1$ (CBAxC57B1) males, 20–22 g | $10^8$ | Control 10.0 100.0 | 7.90)0.22 7.90)0.30 6.90)0.14 | 0.001 | 8.20)0.20 8.25)0.27 8.30)0.38 | |

[1] 6 animals in a group

TABLE 4

INOSIPLEX EFFECT ON HEMAGGLUTININ (HA) TITER IN SERUM OF LINE CBA MICE IMMUNISED WITH SUBOPTIMUM SHEEP ERYTHROCYTE DOSE

| Day after immunisation | Mouse sex, weight, number in a group | Dose (mg/kg) | HA TITER $\frac{\text{(median)}}{M \pm m}$ | | P< |
|---|---|---|---|---|---|
| | | | Control | Inosiplex | |
| 7th day | Males, 20–22 g, n = 10 | 0.5 | $\frac{8.0}{8.10 \pm 0.48}$ | $\frac{8.0}{8.20 \pm 0.35}$ | |
| | Males, 20–22 g, n = 10 | 5.0 | $\frac{9.0}{8.80 \pm 0.49}$ | $\frac{9.0}{9.17 \pm 0.24}$ | |

TABLE 4-continued

INOSIPLEX EFFECT ON HEMAGGLUTININ (HA) TITER IN SERUM OF LINE CBA MICE IMMUNISED WITH SUBOPTIMUM SHEEP ERYTHROCYTE DOSE

| Day after immunisation | Mouse sex, weight, number in a group | Dose (mg/kg) | HA TITER $\frac{\text{(median)}}{M \pm m}$ Control | HA TITER $\frac{\text{(median)}}{M \pm m}$ Inosiplex | P< |
|---|---|---|---|---|---|
| | Males, 20–22 g, n = 12 | 25.0 | $\frac{7.5}{7.67 \pm 0.31}$ | $\frac{7.0}{7.30 \pm 0.21}$ | |
| 14th day | Males, 20–22 g, n = 8 | 250.0 | 7.5 | 8.5 | 0.02 |

P — validity of deviation from the control

TABLE 5

ROPREN ON CELLULAR IMMUNITY REACTION DEVELOPMENT IN MICE[1]

| Reaction type | Administration route | Mouse line, sex, weight | REACTION INDEX (M)m Control | 10 mg/kg | P< | 100 mg/kg | P< |
|---|---|---|---|---|---|---|---|
| DSR | Single intraperitoneal dose | C57B1/6, males, 20–22 g | 28.5)3.1 | 23.2)2.1 | | 24.6)2.9 | |
| " | Single intraperitoneal dose | CBA, males, 19–21 | 17.2)1.5 | 21.3)2.9 | | 22.2)2.4 | |
| " | Per os, for 5 days | C57B1/6, males, 20–22 g | 45.7)3.7 | 46.8)4.7 | | 35.3)3.1 | 0.05 |
| " | Per os, for 5 days | C57B1/6, males, 20–22 g | 36.2)4.3 | 31.2)3.6 | | 25.8)3.3 | 0.05 |
| " | Per os, for 5 days | CBA, males, 20–22 g | 19.1)2.0 | 19.0)1.8 | | 17.5)1.5 | |
| GVHR | Single intraperitoneal dose | $F_1$ (CBAxc57B1) males, 18–20 g | 1.8)0.2 | 2.2)0.2 | | 2.0)0.1 | |
| " | Single intraperitoneal dose | $F_1$ (CBAxc57B1) males, 18–20 g | 2.6)0.2 | 2.5)0.2 | | 2.6)0.3 | |
| " | Per os, for 5 days | $F_1$ (CBAxc57B1) males, 18–20 g | 3.9)0.4 | 3.7)0.4 | | 3.7)0.4 | |

[1] 8 animals in a group

TABLE 6

INOSIPLEX EFFECT ON CELLULAR IMMUNITY REACTION DEVELOPMENT IN MICE[1]

| Reaction type | Mouse line, sex, weight | Dose, mg/kg | REACTION INDEX, % (M)m Control | Inosiplex | P< |
|---|---|---|---|---|---|
| DSR | C57B1/6, males, 18–20 g | 0.5 | 20.6)2.70 n = 6 | 13.9)2.41 n = 4 | |
| | | 5.0 | 26.8)2.33 n = 8 | 27.2)2.38 n = 8 | |
| | | 50.0 | 19.4)1.34 n = 7 | 22.58)2.44 n = 5 | 0.05 |
| " | CBA, males, 18–20 g | 0.5 | 12.1)1.4 n = 8 | 11.9)0.8 n = 9 | |
| | | 5.0 | 9.02)1.09 n = 10 | 8.9)0.89 n = 9 | |
| | | 50.0 | 23.7)1.25 n = 7 | 25.7)2.57 n = 6 | 0.05 |
| GVHR | $F_1$ (CBAxC57B1/6) | 0.5 | 2.12)0.21 n = 9 | 2.35)0.18 n = 8 | |
| | | 5.0 | 2.04)0.19 n = 10 | 2.51)0.15 n = 10 | |
| | | 50.0 | 3.66)0.31 n = 10 | 2.66)0.31 n = 10 | 0.05 |

[1] 6 animals in a group

TABLE 7

ROPREN EFFECT ON PHAGOCYTIC ACTIVITY OF PERITONEAL MACROPHAGES[1]

| N° | Administration route | Dose mg/kg | Phagocyting cells %, (M)m) | P< | Phagocytosis index (M)m) | P< | Phagocytosis index (M)m) | P< |
|---|---|---|---|---|---|---|---|---|
| 1. | Single intraperitoneal dose | Control | 64.1)6.4 | | 12.4)1.0 | | 37.1)4.1 | |
| | | 10.0 | 71.7)3.4 | | 14.8)2.8 | | 68.7)3.4 | 0.001 |
| | | 100.0 | 73.2)0.6 | | 12.0)3.7 | | 49.0)1.8 | 0.05 |
| 2. | " | Control | 49.2)5.1 | | 24.4)4.1 | | 29.0)5.7 | |
| | | 10.0 | 48.2)7.1 | | 10.5)0.44 | 0.02 | 71.3)1.4 | 0.001 |
| | | 100.0 | 48.8)5.0 | | 17.9)2.7 | | 65.6)1.6 | 0.01 |
| 3. | Per os, for 5 days | Control | 56.6)6.2 | | 7.7)0.6 | | 30.9)2.4 | |
| | | 10.0 | 63.0)3.7 | | 8.7)1.4 | | 28.9)2.5 | |
| | | 100.0 | 72.5)3.6 | 0.05 | 8.0)1.1 | | 17.8)2.6 | |
| 4. | " | Control | 56.0)5.7 | | 7.0)0.9 | | 13.5)5.1 | |
| | | 10.0 | 61.0)3.9 | | 8.3)0.7 | | 24.5)5.5 | |
| | | 100.0 | 68.7)1.3 | 0.05 | 0.3)1.1 | | 31.4)12.8 | 0.02 |
| 5. | " | Control | 60.5)3.62 | | 7.7)1.0 | | 23.3)5.1 | |
| | | 10.0 | 75.3)4.0 | 0.05 | 6.2)0.8 | | 19.4)0.9 | |
| | | 100.0 | 80.8)1.6 | 0.01 | 5.0)0.6 | | 35.8)1.8 | |

[1] 6 animals in a group

TABLE 8

INOSIPLEX EFFECT ON PHAGOCYTIC ACTIVITY OF PERITONEAL MACROPHAGES IN LINE F1 (CBA × C57/6) MICE (Males, weight 20–22 g)

| | | Phagcytosis index, % (M)m) | | |
|---|---|---|---|---|
| Dose, mg/kg | Number of animals in groups | Control | Inosiplex | Stimulation degree, % |
| 0.5 | 7 | 37.1)2.8 | 29.7)7.8 | |
| 5.0 | 6 | 37.7)3.2 | 52.4)3.9 P < 0.02 | 39 |
| 50.0 | 6 | 36.0)8.2 | 63.5)4.5 P < 0.05 | 76 |

P – validity of deviation from the control

TABLE 9

ROPREN EFFECT ON INK CLEARANCE IN LINE CBA MICE

| N° Administration route | Dose, mg/kg | Phagocytosis index (M)m) | P< |
|---|---|---|---|
| 1. Single intraperitoneal dose | Control | 4.85)0.19 | |
| | 10.0 | 4.63)0.24 | |
| | 100.0 | 4.71)0.09 | 0.05 |
| 2. ditto | Control | 3.96)0.1 | |
| | 10.0 | 4.04)0.1 | |
| | 100.0 | 4.38)0.28 | 0.05 |
| 3. Per os, for 5 days | Control | 4.22)0.13 | |
| | 10.0 | 4.01)0.18 | |
| | 100.0 | 3.70)0.20 | 0.05 |
| 4. ditto | Control | 4.52)0.14 | |
| | 10.0 | 4.46)0.15 | |
| | 100.0 | 4.58)0.27 | 0.5 |

TABLE 10

INOSIPLEX EFFECT ON INK CLEARANCE[1]

| Dose, mg/kg | Compound | True phagocytosis index | P < |
|---|---|---|---|
| 0.5 | Control | 5.20)0.20 | |
| | Inosiplex | 5.00)0.16 | 0.05 |
| 5.0 | Control | 5.56)0.26 | |
| | Inosiplex | 5.59)0.18 | 0.05 |
| 50.0 | Control | 5.44)0.30 | |
| | Inosiplex | 5.70)0.18 | 0.05 |

[1] Investigation made on line F1 (CBA × C57 B1), 7 animals in a group

TABLE 11

ROPREN EFFECT ON BLOOD SERUM COMPLEMENT ACTIVITY IN LINE F1(CBA × C57B1/6) MICE[1]

| | | Complement activity, CH50/ml | |
|---|---|---|---|
| N° Administration route | Dose, mg/kg | Direct activation pathway | Alternative activation pathway |
| 1. Intraperitoneal | Control | 20.0 | 25.0 |
| | 10.0 | 25.0 | 25.0 |
| | 100.0 | 25.0 | 33.3 |
| 2. Per os, for 5 days | Control | 16.7 | 20.0 |
| | 10.0 | 14.3 | 20.0 |
| | 100.0 | 16.7 | 14.3 |

[1] Serum pool of 5 mice was used for analysis in each group

TABLE 12

ROPREN EFFECT ON IMMUNE SYSTEM OF STRESSED MICE

| Immunoreactivity index, unit of measurement | Date of experiment | Intact animals | STRESSED ANIMALS | | | |
|---|---|---|---|---|---|---|
| | | | Control (0.025% twin) | P1< | Experiment (prenols, 100 mg/kg) | $P_2<$ |
| AFC per $10^6$ cells per spleen (M)m) | 11.05-26.05.87 | 4.8(5.4 ÷ 4.3) 1000(1122 ÷ 891) | 2.4(2.8 ÷ 2.0) 398(490 ÷ 324) | 0.01 0.001 | 6.5(6.6 ÷ 6.3) | 0.001 0.01 |
| HA titer on the 14th day (M)m) | 11.05-4.06.87 | 5.4)0.2 | 4.3)0.1 | 0.001 | 5.0)0.4 | |
| DSR (M)m of reaction index) | 11.05-27.05.87 | 20.4)1.9 | 24.5)3.33 | | 25.3)2.8 | |
| GVHR (M)m of reaction index) | 11.05-28.05.87 | 2.06)0.12 | 1.96)0.14 | | 2.08)0.11 | |
| Phagocytosis Phagocytic index (M)m) | 15.05-29.05.87 | 13.8)3.6 | 16.4)3.2 | | 16.0)2.0 | |
| Phagocytosis completion index, % (M)m) | 15.05-29.05.87 | 37.3)7.4 | 16.8)3.5 | 0.05 | 34.6)5.1 | 0.01 |
| Ink clearence index (M)m) | 11.05-27.05.87 | 4.32)0.1 | 3.02)0.23 | 0.01 | 3.60)0.01 P1 < 0.01 | |

P1 - validity of deviations from indices of intact animals
$P_2$ - validity of deviations from indices of stressed animals

What is claimed is:

1. A method for the treatment of depression caused by chronic emotional stress and of acquired or genetically pre-determined immundeficient state diseases which comprises administering a dosage effective amount of ropren-plant polyprenols represented by Formula (I):

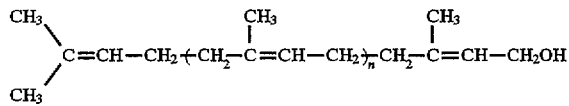

wherein n is from about 8 to about 18, to a mammal suffering from depression due to chronic emotional stress or from an acquired or genetically determined immundeficient disease state.

2. The method of claim 1 wherein the polyprenols are derived from arboreal foliage.

3. The method of claim 1 wherein the polyprenols derived from ropren comprises a chain of about fifty or more carbon atoms.

* * * * *